US007037901B1

(12) United States Patent
Chen

(10) Patent No.: US 7,037,901 B1
(45) Date of Patent: May 2, 2006

(54) RADIOSENSITIZATION BY INDOLOCARBAZOLE DERIVATIVES

(75) Inventor: Allan Y. Chen, Sacramento, CA (US)

(73) Assignee: University of California, Davis, CA (US)

( * ) Notice: Subject to any disclaimer, the term of this patent is extended or adjusted under 35 U.S.C. 154(b) by 148 days.

(21) Appl. No.: 10/075,718

(22) Filed: Feb. 12, 2002

Related U.S. Application Data

(60) Provisional application No. 60/268,224, filed on Feb. 12, 2001.

(51) Int. Cl.
 *A61K 31/70* (2006.01)
 *A61K 31/40* (2006.01)

(52) U.S. Cl. .......................... 514/43; 514/410; 514/416

(58) Field of Classification Search ................... 514/43
 See application file for complete search history.

(56) References Cited

OTHER PUBLICATIONS

Prudhomme "Recent Developments of Rebeccamycin Analogues as Topoisomerase I inhibitors and Antitumor Agents" Current Medicinal Chemistry, 2000, 7, pp. 1189-1212.*
Chen et al. "Mammalian DNA Topoisomerase I Mediates the Enhancement of Radiation Cytotoxicity by Campotothecin Derivatives" Cancer Research 57, pp. 1529-1536, Apr. 15, 1997.*
Carter et al. Chemotherapy of Cancer, Second Edition. 1981. pp. 361-363, 365.*
C. Bailly, et al., "The Camptothecin-Resistant Topoisomerase I Mutant F361S is Cross-Resistant to Antitumor Rebeccamycin Derivatives. A Model for Topoisomerase I Inhibition by Indolocarbazoles," Biochemistry, vol. 38, pp. 8605-8611 (1999).
T. Yoshinari, et al., "Induction of Topoisomerase I-Mediated DNA Cleavage by a New Indolcarbazole, ED-110," Cancer Res, vol. 53, pp. 490-494 (1990).
Christian Bailly, et al., "Recognition of Specific Sequences in DNA by a Topoisomerase I Inhibitor Derived from the Antitumor Drug Rebeccamycin," Molecular Pharmacology, vol. 53, Issue 1, pp. 77-87 (1998).
Christian Bailly, et al., "Enhanced Binding to DNA and Topoisomerase I Inhibition by an Analog of the Antitumor Antibiotic Rebeccamycin Containing an Amino Sugar Residue," Molecular Pharmacology, vol. 55, Issue 2, pp. 377-385 (1999).
E.R. Pereira, et al., "Structure-activity Relationships in a Series of Substituted Indolocarbazoles: Topoisomerase I and Protein Kinase C Inhibition and Antitumoral and Antimicrobial Properties," J Med Chem, vol. 39, pp. 4471-4477 (1996).
Emmanuel Labourier, et al., "Poisoning of Topoisomerase I by an Antitumor Indolocarbazole Drug," Cancer Research, vol. 59, pp. 52-55 (1999).
F. Anizon, et al., "Syntheses and Biological Activities (Topoisomerase Inhibition and Antitumor and Antimicrobial Properties) of Rebeccamycin Analogues Bearing Modified Sugar Moieties and Substituted on the Imide Nitrogen with a Methyl Group," J Med Chem, vol. 40, pp. 3456-3465 (1997).
P. Moreau, et al., "Syntheses and Biological Evaluation of Indolocarbazoles, Analogues of Rebeccamycin, Modified at the Imide Heterocycle," J Med Chem, vol. 41, pp. 1631-1640 (1998).
P. Moreau, et al., "Synthesis, Mode of Action, and Biological Activities of Rebeccamycin Bromo Derivatives," J Med Chem, vol. 42, pp. 1816-1822 (1999).
A. Tanizawa, et al., "Topoisomerase I Alteration in a Camptothecin-Resistant Cell Line Derived from Chinese Hamster DC3F Cells in Culture," Cancer Res, vol. 52, pp. 1848-1854 (1992).
A. Tanizawa, et al., "Cloning of Chinese Hamster DNA Topoisomerase I cDNA and Identification of a Single Point Mutation Responsible for Camptothecin Resistance," J Biol Chem, vol. 268, pp. 25463-25468 (1993).
N. Albright, "Computer Programs for the Analysis of Cellular Survival Data," Radiat Res, vol. 112, pp. 331-340 (1987).

(Continued)

*Primary Examiner*—Sreeni Padmanabhan
*Assistant Examiner*—Jennifer Kim
(74) *Attorney, Agent, or Firm*—Morgan Lewis & Bockius LLP

(57) ABSTRACT

The present invention is based on the discovery of a composition that provides radiosensitization effect. Specifically the composition contains an indolocarbazole derivative. The present invention provides methods for radiosensitizing neoplastic cells using indolocarbazole derivatives and methods for treating neoplastic cells using indolocarbazole derivatives in combination with radiation or radiation and chemotherapy.

6 Claims, 5 Drawing Sheets

OTHER PUBLICATIONS

YN Chen, et al., "Characterization of Adriamycin-Resistant Human Breast Cancer Cells which Display Overexpression of a Novel Resistance-Related Membrane Protein," J Biol Chem, vol. 265, pp. 10073-10080 (1990).

D. Subramanian, et al., "Analysis of Topoisomerase I/DNA Complexes in Patients Administered Topotecan," Cancer Res, vol. 55, pp. 2097-2103 (1995).

Corinne Pondarré, et al., "In vivo Sequencing of Camptothecin-Induced Topoisomerase I Cleavage Sites in Human Colon Carcinoma Cells," Nucleic Acids Research, vol. 25, pp. 4111-4116 (1997).

L.L. Herscher, et al., "Principles of Chemoradiation: Theoretical and Practical Considerations," Oncology (Huntingt), vol. 13, pp. 11-22 (1999).

Allan Y. Chen, et al., "p53 and p21 Are Major Cellular Determinants for DNA Topoisomerase I-Mediated Radiation Sensitization in Mammalian Cells," Annals of the New York Academy of Sciences, vol. 922, pp. 298-300 (2000).

Zezhang T. Wen, et al., "Functional Genomics Approach to Identifying Genes Required to Biofilm Development by *Streptococcus mutans*," Applied and Environmental Microbiology, vol. 68, No. 3, pp. 1196-1203 (2002).

Paul E. Kolenbrander, et al., "Intergeneric Coaggregation of Oral *Treponema* spp. With *Fusobacterium* ssp. And Intrageneric Coaggregation among *Fusobacterium* spp.," Infection and Immunity, vol. 63, No. 12, pp. 4584-4588 (1995).

Karsten R. O. Hazlett, et al., "Inactivation of the *gbpA* Gene of *Streptococcus mutans* Alters structural and Functional Aspects of Plaque Biofilm which are Compensated by Recombination of the *gtfB* and *gtfC* Genes," Infection and Immunity, vol. 67, No. 8, pp. 3909-3914 (1999).

Renata O. Mattos-Graner, et al., "Cloning of the *Streptococcus mutans* Gene Encoding Glucan Binding Protein B and Analysis of Genetic Diversity and Protein Production in Clinical Isolates," Infection and Immunity, vol. 69, No. 11, pp. 6931-6941 (2001).

Leslie A. Pratt, et al., "Genetic Analyses of Bacterial Biofilm Formation," Current Opinion in Microbiology, vol. 2, pp. 598-603 (1999).

Gary M. Dunny, et al., "Cell-Cell Communication in Gram-Positive Bacteria," Annu. Rev. Microbiol., vol. 51, pp. 527-564 (1997).

Elizabeth A. Joyce, et al., "Evidence for a Signaling System in *Helicobacter pylorf*: Detection of a *luxS* -Encoded Autoinducer," Journal of Bacteriology, vol. 182, No. 13, pp. 3638-3643 (2000).

Mark H. Forsyth, et al., "Intercellular Communication in *Helicobacter pylort*: *luxS* Is Essential for the Production of an Extracellular Signaling Molecule," Infection and Immunity, vol. 68, No. 6, pp. 3193-3199 (2000).

S. N. Ruzheinikov, et al., The 1.2 A Structure of a Novel Quorum-Sensing Protein, *Bacillus subtilis* LuxS, J. Mol. Biol., vol. 313, pp. 111-122 (2001).

Stephan Schauder, et al., The LuxS Family of Bacterial Autoinducers: Biosynthesis of a Novel Quorum-Sensing Signal Molecule, Molecular Biology, vol. 41, Issue 2, pp. 463-476 (2001).

Michael G. Surette, et al., "Quorum Sensing in *Escherichia coli, Salmonella typhimuruium* and *Vibrio harveyi*: A New Family of Genes Responsible for Autoinducer Production," Proc. Natl. Acad. Sci. USA, vol. 96, pp. 1639-1644 (1999).

Mary Ellen Davey, et al., "Microbial Biofilms: form Ecology to Molecular Genetics," Microbiology and Molecular Biology Reviews, pp. 847-867 (2000).

Ping Chen, et al., "The Specific Genes for Lantibiotic Mutacin II Biosynthesis in *Streptococcus mutans* TB Are Clustered and Can Be Transferred En Bloc," Applied and Environmental Microbiology, pp. 1356-1360 (1999).

Fengxia QI, et al., "Purification of Mutacin III from Group III *Streptococcus mutans* UA787 and Genetic Analyses of Mutacin III Biosynthesis Genes," Applied and Environmental Microbiology, vol. 65, No. 9, pp. 3880-3887 (1999).

* cited by examiner

| INDO derivative | $R_1$ | $R_2 = R_3$ |
|---|---|---|
| F1 (rebeccamycin) | NH | Cl |
| F5 | O | H |
| F7 (also known as R-3) | NOH | H |
| F43 | NCH$_3$ | Cl |
| F44 | NCH$_3$ | H |
| F71 | NH | H |

| Parameters | RT alone | F1 | F5 | F7 | CPT |
|---|---|---|---|---|---|
| $D_0$ | 1.8 | 1.8 | 1.8 | 1.5 | 1.8 |
| $D_q$ | 2.7 | 0.0 | 0.0 | 0.7 | 0.8 |

RADIOSENSITIZATION BY INDOLOCARBAZOLE DERIVATIVES

CROSS REFERENCE TO RELATED APPLICATIONS

This application claims priority under 35 U.S.C. 119(e)(1) to U.S. Provisional Application No. 60/268,224 filed on Feb. 12, 2001 and entitled "Indolocarbazole Derivatives and Methods of Use Thereof", which is incorporated herein by reference.

FIELD OF THE INVENTION

This invention relates generally to the field of radiosensitization, especially using indolocarbazole derivatives to enhance the radiation effect.

BACKGROUND OF THE INVENTION

Combined modality therapy with chemotherapy and radiation has been frequently used in treating various kinds of human cancers. There are at least three major advantages to combine chemotherapy with radiation therapy for treating cancers. First, by offering systemic control over metastatic disease, chemotherapy complements radiation therapy's pivotal role in providing local control over the primary tumor.

Second, chemotherapy may contribute in local control by reducing the chemo-sensitive subpopulation of the primary tumor. Third, some chemotherapeutic drugs can enhance the cytotoxic effect of low-LET (linear energy transfer) radiation (such as photons and electrons), and therefore, improve the treatment efficacy toward the irradiated tumors. Indeed, numerous randomized clinical trials, conducted in various clinical settings, have shown a superior treatment efficacy of combination chemoradiation than either modality alone. However, the efficacy of various chemoradiation regimens is still largely limited by the cumulative normal tissue toxicity from combining two modalities.

A better understanding of the mechanism of cytotoxic interaction between chemotherapy and radiation and the development of new drugs that can enhance radiation cytotoxicity selectively toward cancer cells are among the major challenges for cancer researchers.

The catalytic activity of DNA topoisomerase I (TOP1) is important for many aspects of nucleic acid metabolism including DNA replication elongation, transcription elongation of RNA and regulation of DNA supercoiling. Mammalian TOP1 is also a major cellular target of an increasing number of anticancer drugs, including camptothecin derivatives, DNA minor groove-binding drugs such as Hoechst 33342 and nogalamycin, and indolocarbazole (INDO) derivatives.

Instead of direct inhibition of catalytic enzyme activity, TOP1 drugs kill cells by converting an essential DNA topology modifying activity into a DNA breaking poison, which damages DNA through interactions with cellular processes such as replication of DNA. The presence of elevated TOP1 levels in both proliferating and quiescent tumor cells has rendered TOP1 a favored selective target for anticancer therapy.

INDO derivatives represent a new class of TOP1 drugs. A number of INDO derivatives have been demonstrated to exert their cytotoxic effects through the TOP1-mediated mechanism similar to that of the camptothecin derivatives. Also, based on its cross-resistance toward a camptothecin-resistant mutant TOP1, the INDO derivative R-3 has been proposed to share common steric and electronic features with camptothecin (Bailly, C., et al., Biochemistry, 38:8605–8611, (1999)). However, many INDO derivatives interact with DNA with a higher affinity than camptothecin derivatives (Yoshinari, T., Cancer Res., 53:490–494 (1993); Bailly, C., Mol Pharmacol., 53:77–87 (1998); and Bailly, C., et al., Mol Pharmacol., 55:377–385 (1999)). In addition, some structural derivatives of INDO possess other biological activities including inhibitory effects toward protein kinase C (Bailly, C., et al., Mol Pharmacol., 55:377–385 (1999), and Pereira, E. R., et al., J. Med. Chem., 39:4471–4477 (1996)), protein kinase A (Pereira, E. R., et al., J. Med. Chem., 39:4471–4477 (1996)) and TOP1 kinase (Labourier, E., et al., Cancer Res., 59:52–55 (1999); Anizon, F., et al., J. Med. Chem., 40:3456–3465 (1997)); Moreau, P., et al., J. Med. Chem., 41:1631–1640 (1998); and Moreau, P., et al., J. Med. Chem., 42:1816–1822 (1999)). Notably, the inhibitory activity of TOP1 kinase of the INDO derivative R-3 appears to be distinct from its ability to induce TOP1-mediated DNA cleavage (Labourier, E., et al., Cancer Res., 59:52–55 (1999)).

There is a need in the field to develop more agents that are capable of inducing radiosensitization, especially at a non-cytotoxic level.

SUMMARY OF THE INVENTION

The present invention is based on the discovery that indolocarbazole derivatives can be used for radiosensitization, especially at a non-cytotoxic level. Accordingly, the present invention provides methods of inducing radiosensitization of neoplastic cells by using indolocarbazole derivatives and methods for treating neoplastic cells by using indolocarbazole derivatives in combination with radiation or radiation and chemotherapy.

In one embodiment, the present invention provides a method for enhancing the radiosensitivity of a neoplastic cell. The method includes contacting the neoplastic cell with a radiosensitivity increasing amount of an indolocarbazole derivative having the following structure A

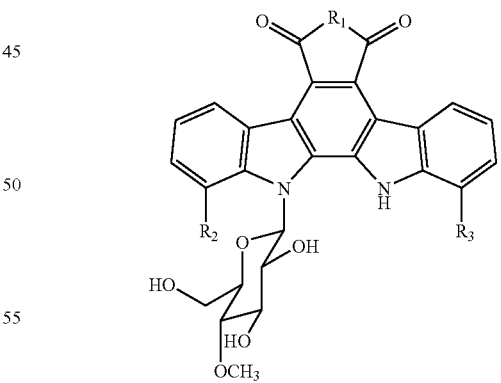

wherein $R_1$ is not $NCH_3$ and wherein $R_2$ and $R_3$ are not H when $R_1$ is NH.

In another embodiment, the present invention provides a method for enhancing the radiosensitivity of a neoplastic cell. The method comprises contacting the neoplastic cell with a radiosensitivity increasing amount of a composition comprising an indolocarbazole derivative having the following structure A

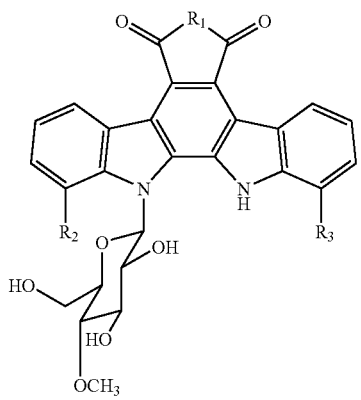

wherein $R_1$ is not $NCH_3$ and wherein $R_2$ and $R_3$ are not H when $R_1$ is NH.

In yet another embodiment, the present invention provides a method for treating a neoplastic cell. The method comprises contacting the neoplastic cell with a radiosensitivity increasing amount of an indolocarbazole derivative having the following structure A

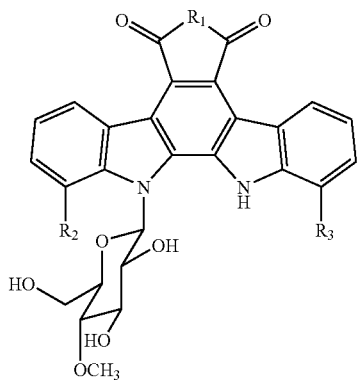

wherein $R_1$ is not $NCH_3$ and wherein $R_2$ and $R_3$ are not H when $R_1$ is NH and contacting the neoplastic cell with radiation or radiation in combination with an anti-neoplastic chemotherapeutic agent.

In still another embodiment, the present invention provides a method for treating a neoplastic cell. The method comprises contacting the neoplastic cell with a radiosensitivity increasing amount of a composition comprising an indolocarbazole derivative having the following structure A

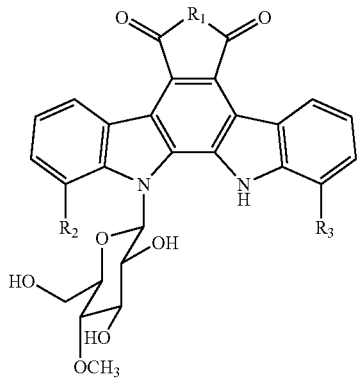

wherein $R_1$ is not $NCH_3$ and wherein $R_2$ and $R_3$ are not H when $R_1$ is NH and contacting the neoplastic cell with radiation or radiation in combination with an anti-neoplastic chemotherapeutic agent.

In another embodiment, the present invention provides a method for treating a neoplastic growth. The method comprises administering to a subject in need of such treatment a radiosensitivity increasing amount of an indolocarbazole derivative having the following structure A

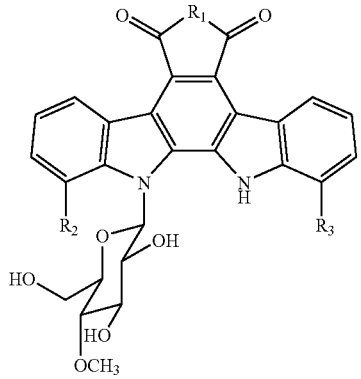

wherein $R_1$ is not $NCH_3$ and wherein $R_2$ and $R_3$ are not H when $R_1$ is NH, and radiation or radiation in combination with an anti-neoplastic chemotherapeutic agent.

In yet another embodiment, the present invention provides a method for treating a neoplastic growth. The method comprises administering to a subject in need of such treatment a radiosensitivity increasing amount of a composition comprising an indolocarbazole derivative having the following structure A

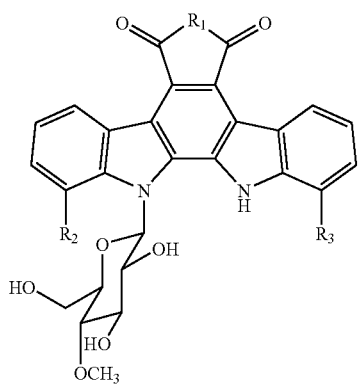

wherein $R_1$ is not $NCH_3$ and wherein $R_2$ and $R_3$ are not H when $R_1$ is NH, and radiation or radiation in combination with an anti-neoplastic chemotherapeutic agent.

SUMMARY OF THE FIGURES

FIG. 4A shows the gel which was initially stained with ethidium bromide (1 μg/ml), washed and photographed under UV light. FIG. 4B shows the separation of the "nicked" from the "relaxed" DNA population by running the gel in FIG. 4A for another 4 h in the presence of ethidium bromide before being photographed. FIG. 4C shows the intensity of the nicked DNA of each lane from FIG. 4B which was measured using the ImageJ program. The intensity of the nicked band of each lane was plotted after the background intensity (pHOT1+TOP1 lane) was subtracted.

DESCRIPTION OF THE PREFERRED EMBODIMENTS

Figure 1:
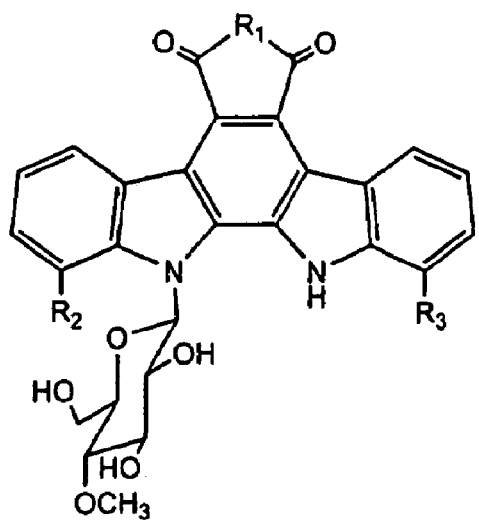
FIG. 1 shows chemical structures of indolocarbazole derivatives used in this study.

The present invention relates in general to radiosensitization using indolocarbazole derivatives. It is the discovery of the present invention that indolocarbazole derivatives can make cells radiosensitive or increase their radiosensitivity, especially at a non-cytotoxic level. Accordingly, the present invention provides methods for enhancing the radiosensitivity of cells, especially neoplastic cells by contacting the cells with a radiosensitivity increasing amount of one or more indolocarbazole derivatives.

Indolocarbazole derivatives used in the present invention can be any compound having the following structure A

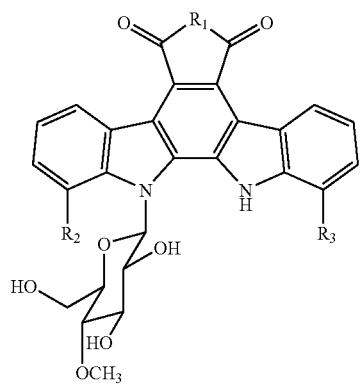

According to one embodiment of the present invention, $R_1$, $R_2$, and $R_3$ can be any chemical group, provided that $R_1$ is not $NCH_3$ and $R_2$ and $R_3$ are not H when $R_1$ is NH. Specifically in one embodiment, $R_1$ is NH, O, or NOH while $R_2$ and $R_3$ are the same and are either Cl or H, provided that $R_2$ and $R_3$ are not H when $R_1$ is NH. For example, the indolocarbazole derivatives used in the present invention can be F1(rebeccamycin), F5, or F7 (also known as R-3).

In another embodiment, $R_1$, $R_2$, and $R_3$ can be any chemical group provided that the compound is a DNA topoisomerase I (TOP1)-targeted compound. In still another embodiment, $R_1$, $R_2$, and $R_3$ can be any chemical group provided that the compound is capable of inducing sublethal DNA damage, e.g., obliteration of the "shoulder" of the radiation survival curve induced by the compound.

According to one feature of the present invention, the indolocarbazole derivatives of the present invention can be used in combination with radiation or radiation and chemotherapy to treat neoplastic cells. For example, neoplastic cells can be contacted with or exposed to the indolocarbazole derivatives of the present invention before, during, or after being irradiated with radiation. In one embodiment, the indolocarbazole derivatives of the present invention is delivered to neoplastic cells prior to radiation, e.g., 0.5 to 2 hours prior to being irradiated.

Contacting cells with the indolocarbazole derivatives of the present invention can be carried out in any suitable way either in vitro or in vivo. For example, the cells can be contacted with or exposed to indolocarbazole derivatives of the present invention either in tissue cultures or in a subject, e.g., mammalian such as human. The neoplastic cells of the present invention can be any cells of abnormal growth. In one embodiment, the neoplastic cells are from a solid tumor or cancer. For example, the neoplastic cells to be radiosensitized or treated can be prostate cancer cells, bone cancer cells, colon cancer cells, lymphoma cancer cells, or brain cancer cells.

According to one embodiment of the present invention, indolocarbazole derivatives of the present invention can be used at a non-cytotoxic level to radiosensitize or treat cells, especially neoplastic cells. For example, indolocarbazole derivatives of the present invention can be used at low concentrations, e.g., 2 μg/ml that is not cytotoxic while effective in inducing radiosensitization.

The indolocarbazole derivatives of the present invention can be used in a pharmaceutical composition comprising one or more indolocarbazole derivatives and a pharmaceutically acceptable carrier. Pharmaceutically acceptable carriers are well known to those in the art. Such carriers include, but are not limited to, large, slowly metabolized macromolecules, such as proteins, polysaccharides, polylactic acids, polyglycolic acids, polymeric amino acids, amino acid copolymers, and inactive virus particles.

Pharmaceutically acceptable carriers can also be pharmaceutically acceptable salts such as hydrochlorides, hydrobromides, phosphates, or sulfates, as well as the salts of organic acids such as acetates, proprionates, malonates, or benzoates. The composition can also contain liquids, such as water, saline, glycerol, and ethanol, as well as substances such as wetting agents, emulsifying agents, or pH buffering agents.

The indolocarbazole derivatives of the present invention can be administered alone, in a composition with a suitable pharmaceutical carrier, or in combination with radiation, radiation and chemotherapy, or other therapeutic agents. A radiosensitivity increasing amount of the indolocarbazole derivatives of the present invention or a composition containing the indolocarbazole derivatives of the present invention can be any amount that increases neoplastic cells' sensitivity to regular radiation therapy or induces radiosensitization of neoplastic cells. Usually a radiosensitivity increasing amount can be determined on a case-by-case basis. Factors should be considered generally include age, body weight, type of the neoplastic cells, stage of the condition, other disease conditions, duration of the treatment, and the response to the initial treatment.

In one embodiment, a radiosenstivity increasing amount is an amount that increases the radiosenstitivity and induces only "sublethal damages" of cells or induces none or minimum cytotoxicity. In another embodiment, a radiosensitivity increasing amount can be an amount that provides at least 1, 2, 5, or 10 μg/ml at the neoplastic locus.

Typically, the indolocarbazole derivatives of the present invention are prepared as an injectable, either as a liquid solution or suspension. However, solid forms suitable for solution in, or suspension in, liquid vehicles prior to injection can also be prepared. The indolocarbazole derivatives of the present invention can also be formulated into an enteric-coated tablet or gel capsule according to known methods in the art.

The indolocarbazole derivatives and the compositions thereof used in the present invention may be administered in any way which is medically acceptable which may depend on the disease condition or injury being treated. Possible administration routes include injections, by parenteral routes such as intravascular, intravenous, intraepidural or others, as well as oral, nasal, ophthalmic, rectal, topical, or pulmonary, e.g., by inhalation. The indolocarbazole-derivatives and the compositions thereof may also be directly applied to tissue surfaces. Sustained release administration is also specifically included in the invention, by such means as depot injections or erodible implants.

EXAMPLES

The following examples are intended to illustrate but not to limit the invention in any manner, shape, or form, either explicitly or implicitly. While they are typical of those that might be used, other procedures, methodologies, or techniques known to those skilled in the art may alternatively be used.

In the current study, we investigated whether INDO derivatives induced radiosensitization (RS) in cultured mammalian cells. Among the six INDO derivatives tested, we showed that F1, F5 and F7, but not F43, F44 or F71, induced RS in human breast cancer MCF-7 cells. The sensitization enhancement ratios (SERs) induced by F1, F5 and F7 compared favorably to the SER induced by camptothecin, particularly, at a relatively non-cytotoxic concentration of 2 μg/ml. Analyzed by the Single-hit multi-target model, "obliteration of the shoulder" of the radiation survival curve appeared to be the common RS mechanism for F1, F5 and F7. The role of TOP1 in mediating the cytotoxic and radiosensitizing effects of INDO derivatives was characterized.

The six INDO derivatives exhibited varying efficiencies in inducing TOP1-mediated DNA cleavages in vitro, as well as in stabilizing DNA-protein cross-links in vivo with the following order: F71, F7>F44, F1>F5>F43. Interestingly, F71 and F44, which had no detectable radiosensitizing activity in various cultured mammalian cells, were relatively potent in inducing TOP1-mediated DNA damage and cytotoxicity.

The induction of RS by INDO derivatives was further examined in the Chinese hamster DC3F cells and their camptothecin-resistant DC3F/C-10 cells. In comparison to the DC3F cells, the TOP1 mutant DC3F/C-10 cells showed decreased sensitivity to the cytotoxic effect of F7, as well as the radiosensitizing effect of F7 and F1.

Example 1

Materials and Methods

Drugs and Materials. INDO derivatives were synthesized as published previously (Pereira, E. R., et al., J. Med. Chem., 39:4471–4477 (1996); Anizon, F., et al., J. Med. Chem., 40:3456–3465 (1997)); Moreau, P., et al., J. Med. Chem., 41:1631–1640 (1998); and Moreau, P., et al., J. Med. Chem., 42:1816–1822 (1999)). Camptothecin lactone (NSC 94600) and DMSO were purchased from Sigma Chemical Co. (St. Louis, Mo.). All drugs were dissolved in DMSO at a concentration of either 10 μM or 10 μg/ml and kept frozen in aliquots at −20° C. Except for fetal bovine serum, which was obtained from Inovar Biologicals (Gaithersburg, Md.), media and other reagents for tissue culture work were purchased from Gibco (Grand Island, N.Y.). Purified human TOP1 and the pHOT1 plasmid were purchased from the TopoGEN, Inc. (Columbus, Ohio).

Cell Cultures. The human breast cancer MCF-7 cell line was obtained from the American Type Culture Collection (Rockville, Md.) and was grown in RPMI 1640 medium supplemented with 10% heat-inactivated fetal bovine serum.

The Chinese Hamster lung fibroblast DC3F cell line and its camptothecin-resistant DC3F/C-10 subline were kindly provided by Dr. Yves Pommier of the National Cancer Institute (Bethesda, Md.) (Tanizawa, A., et al., Cancer Res., 52:1848–1854 (1992) and Tanizawa, A., et al., J. Biol. Chem., 268:25463–25468 (1993)). These cell lines were grown in Dulbecco's minimal essential medium supplemented with 10% heat-inactivated fetal bovine serum, 2 μM glutamine and 0.1 μM nonessential amino acids as described previously (Tanizawa, A., et al., Cancer Res., 52:1848–1854 (1992) and Tanizawa, A., et al., J. Biol. Chem., 268:25463–25468 (1993)).

The Chinese hamster ovary CHO cells were obtained from Dr. Terence Dermody of the Vanderbilt University Medical School (Nashville, Tenn.) and were grown in Ham's medium supplemented with 10% heat-inactivated fetal bovine serum.

All cell lines were grown as stock cultures maintained at 37° C. in a humidified atmosphere of 5% $CO_2$ and 95% air at pH 7.3. Under these conditions, the doubling times and plating efficiencies for DC3F, DC3F/C-10 and MCF-7 cells were 10 h, 40–50%; 15 h, 45–55%; and 22 h, 50–60%, respectively.

Clonogenic Survival Assay. For a typical clonogenic survival experiment, stock cultures of exponentially growing cells were trypsinized, rinsed, and plated ($5\times10^5$ cells per dish for DC3F and DC3F/C-10 cells; $1\times10^6$ cells for MCF-7 cells) into 100-mm petri dishes and incubated at 37° C. 18–24 h prior to experimental studies.

Following various experimental protocols with drug incubation and irradiation, cells were trypsinized, rinsed, counted, and plated for microscopic colony formation. Depending on the anticipated survival level, $10^2$ to $10^5$ cells were plated per dose point. When higher cell numbers were plated, large petri dishes were used to avoid possible cell-density effect (100-mm instead of 60-mm petri dishes for cell number$\geq 5\times10^4$). Depending on the treatment protocols, an equivalent amount of DMSO was added into each of the control radiation alone dishes (final DMSO concentration <0.1%).

Following seven to fourteen days of incubation, colonies were fixed with methanol/acetic acid (3:1), stained with crystal violet. Colonies consisting of >50 cells were counted. All survival points were done in triplicate, and experiments were conducted a minimum of two times. Error bars shown in the figures represent standard deviations (SD) and are shown when larger than the symbol.

Irradiation of Cells. Drug-treated and control cells in medium were irradiated using a cobalt-60 source (Eldorado 8; Theratronics, Canada) at a dose rate of 105 cGy/min.

Analysis of Survival Curves. Survival curves were corrected for cytotoxicity induced by drug alone treatment. Sensitization enhancement ratios (SERs) and standard deviations for survival curves were determined at 10% cell survival. Each SER was calculated by dividing the radiation dose to induce 10% cell survival in the absence of radiosensitizer with the radiation dose to induce 10% cell survival in the presence of radiosensitizer.

The updated programs developed by Dr. N. Albright (San Rafael, Calif.) (Albright, N., Radiat. Res., 112:331–340 (1987)) were used for curve fitting for MCF-7 cells with the linear quadratic (LQ) and the single hit multi-target (SHMT) models. Both the LQ and SHMT models gave qualitatively good fits. The fit with the SHMT model was used for the present study.

In vitro drug-stimulated TOP1 cleavage assay. Drug-stimulated DNA cleavage assay using purified human TOP1 was performed according to the protocol provided by TopoGEN Inc. (Columbus, Ohio) with modifications.

Briefly, supercoiled pHOT1 plasmid DNA (0.2 μg) was incubated with 1 unit of human TOP1 in cleavage buffer (50 mM Tris, pH 7.8, 50 mM KCl, 10 mM MgCl2, 1 mM dithiothreitol, 1 mM EDTA) in the presence of varying concentrations of the drug under study. Following a 30-min incubation at 37° C., the reactions were terminated by adding SDS to 1.0% and proteinase K to 200 μg/ml. The proteinase K treatment continued at 37° C. for 1 h. The sample was then mixed with loading dye (containing sucrose and bromphenol blue) and separated in 1% agarose gel in 0.08 M Tris-phosphate, 0.008 M EDTA, pH 8.0 buffer at room temperature for 16 h.

The gel was initially stained with ethidium bromide (1 mg/ml), washed and photographed under UV light. In order to separate the "nicked" from the "relaxed" DNA population, the gel was further run for 4 h in the presence of ethidium bromide before being photographed again under UV light. The photograph was scanned and the intensity of the nicked DNA of each lane was measured using the ImageJ program obtained from the National Institutes of Health (web site: rsb.info.nih.gov/ij/). The intensity of the nicked band of each lane was plotted after the background intensity (pHOT1+TOP1 lane) was subtracted.

In vivo $K^+$-SDS co-precipitation assay for protein-DNA cross-links. The $K^+$-SDS co-precipitation assay as described previously (Chen, Y. N., et al., J. Biol. Chem., 265:10073–10080 (1990)) was used to quantify the formation of covalent topoisomerase-DNA cross-links in drug-treated cells.

Briefly, the DNA in logarithmic growing Chinese hamster CHO cells was overnight-labeled in medium containing 1 μCi/ml of [mehtyl-$^3$H] thymidine. These cells were then trypsinized and diluted in fresh medium before aliquoted into a 24-well plate. After overnight incubation, the labeled cells were treated with various concentrations of drugs for 30 min, washed with phosphate-buffered saline once, and lysed by adding 1 ml of prewarmed lysis solution (1.25% SDS, 5 mM EDTA, 0.4 mg/ml salmon sperm DNA, pH 8.0, 65° C.).

Following shearing chromosomal DNA by passing the lysate through a 19-gauge needle, the sample was transferred to a tube containing 0.25 ml of 325 mM KCl. The sample was vortexed vigorously for 10 s, cooled on ice for 10 min and centrifuged at 3000 rpm for 10 min at 4° C.

The pellet was then resuspended in 1 ml of a wash solution (100 mM KCl, 1 mM EDTA, 0.1 mg/ml salmon sperm DNA, 10 mM Tris-HCl, pH 8.0) and placed at 65° C. for 10 min with occasional mixing. The sample was again cooled on ice for 10 min and centrifuged at 3000 rpm for 10 min at 4° C. After the pellet from each sample was washed again, the pellet was finally resuspended in 0.2 ml of 65° C. water and added to 5 ml of scintillation fluid to determine radioactive counts.

The background precipitable counts were obtained by treating the lysate with proteinase K (400 μg/ml) at 65° C. for 2 h. Data are arithmetic means (±SD) of three determinations, and the background counts have been subtracted.

Example 2

Figure 2:
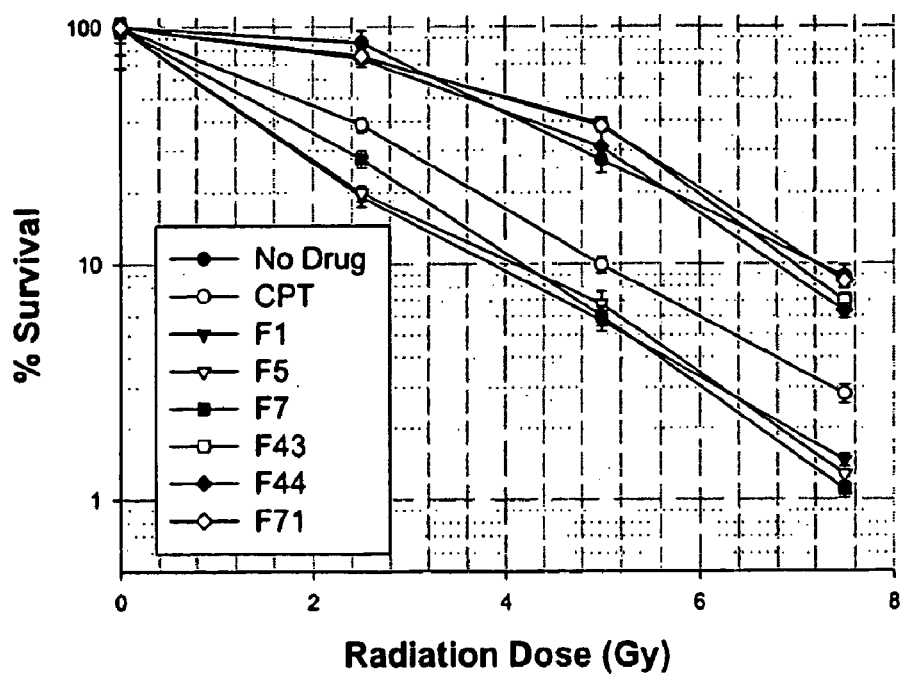
FIG. 2 shows induction of radiosensitization in human breast cancer MCF-7 cells by various indolocarbazole derivatives and camptothecin (CPT). Points, mean of triplicates; bars, SD.

Indolocarbazole (INDO) Derivatives F1, F5 and F7, but not F43, F44 or F71, Induced Radiosensitization (RS) in Human Breast Cancer MCF-7 Cells Six INDO derivatives (see FIG. 1 for their chemical structures) were tested in exponentially growing human breast cancer MCF-7 cells for their cytotoxic and radiosensitizing effects by clonogenic survival assays. As shown in FIG. 2, induction of RS was observed in human breast cancer MCF-7 cells treated with one-hour preincubation with 2 μg/ml of F1, F5 and F7, but not F43, F44 or F71.

As shown in Table 1, the values of sensitization enhancement ratio (SER) of the radiosensitizing F1, F5 and F7 range from 1.7 to 1.9. These values compare favorably to the SER of 1.4 induced by the prototypic TOP1-targeted camptothecin. In contrast, F43, F44 and F71 do not enhance radio-cytotoxicity at 2 μg/ml (FIG. 2, Table 1), or at an even higher concentration of 10 μg/ml (data not shown). Notably, in contrast to the cytotoxic concentration required by camptothecin to induce RS, the INDO derivatives F1, F5 and F7 induce RS in human MCF-7 cells at a relatively non-cytotoxic concentration of 2 μg/ml (Table 1). Indeed, consistent with the results in MCF-7 cells, our preliminary results in Chinese hamster CHO cells also show that F5 is a potent inducer of RS at non-cytotoxic concentrations of 2 μg/ml and 10 μg/ml (data not shown).

TABLE 1

SER values in human MCF-7 cells treated with various indolocarbazole derivatives or camptothecin (CPT) in combination with radiation[a]

| Drug treatment | Percent of cell survival without RT[b] | RT dose (Gy) at 10% survival | ER[c] |
|---|---|---|---|
| No drug | 100 ± 11 | 7.2 | 1.0 |
| F1 | 94 ± 8 | 3.8 | 1.9 |
| F5 | 98 ± 2 | 4.2 | 1.7 |
| F7 | 98 ± 2 | 4.2 | 1.7 |
| F43 | 95 ± 5 | 7.0 | 1.0 |
| F44 | 100 ± 2 | 6.9 | 1.0 |

TABLE 1-continued

SER values in human MCF-7 cells treated with various indolocarbazole
derivatives or camptothecin (CPT) in combination with radiation[a]

| Drug treatment | Percent of cell survival without RT[b] | RT dose (Gy) at 10% survival | ER[c] |
|---|---|---|---|
| F71 | 85 ± 10 | 7.2 | 1.0 |
| CPT | 72 ± 5 | 5.0 | 1.4 |

[a]Clonogenic survival assays as described in "Materials and Methods" were performed in MCF-7 cells. Cells were pre-treated with 2 µg/ml of various indolocarbazole derivatives or 1 µM of camptothecin (CPT) for 1 h, rinsed off the drug, prior to receive radiation treatment.
[b]Percent of cell survival and RT dose at 10% survival were determined graphically from FIG. 2.
[c]SER = the radiation dose to induce 10% cell survival in the absence of drug/the radiation dose to induce 10% cell survival in the presence of drug.

Example 3

F1, F5 and F7 Induce RS by Obliterating the "Shoulder" of the Radiation Survival Curve The updated programs developed and kindly provided by Dr. Albright (Albright, N., Radiat. Res., 1 12:331–340 (1987)) were used for curve fitting of the chemoradiation survival curves with the single-hit multitarget (SHMT) model. Good graphical fits were obtained for curves generated by treating cells with INDO derivatives in combination with radiation.

FIG. 3B shows the respective radiation survival curve parameters. The $D_0$, defined as the radiation dose required for reducing the survival fraction to 37% of its previous value, usually denotes the radiation sensitivity of the cells (Hall, E., 4th ed. pp. 29–43, Philadelphia, J.B. Lippincott Co. (1994)). The Dq, defined as the straight portion of the survival curve extrapolated backward cutting the dose axis drawn through a survival fraction of unity, represents the width of the shoulder of the survival curve Hall, E., 4th ed. pp. 29–43, Philadelphia, J.B. Lippincott Co. (1994)).

As shown in FIG. 3B, no apparent change in the value of $D_0$ was observed among the survival curves treated with various INDO derivatives. However, the value of Dq was drastically reduced in the radiation survival curves generated by treating cells with camptothecin, F1, F5 and F7, but not F43, F44 or F71. Therefore, the observed difference in radiocytotoxicity in the presence of various INDO derivatives is mostly due to obliteration of the "shoulder" of the radiation survival curve and not its terminal slope ($1/D_0$) Hall, E., 4th ed. pp. 29–43, Philadelphia, J.B. Lippincott Co. (1994)).

Example 4

INDO Derivatives Exhibit Varying Efficiencies in Inducing TOP1-Mediated DNA Damage In Vitro In an attempt to determine the involvement of TOP1 in mediating cytotoxic and radiosensitizing effects of the six INDO derivatives, their individual activities in inducing TOP1-mediated DNA damage were characterized by using the in vitro purified human TOP1 enzyme system, as well as the in vivo potassium-SDS co-precipitation assay.

Figure 4:
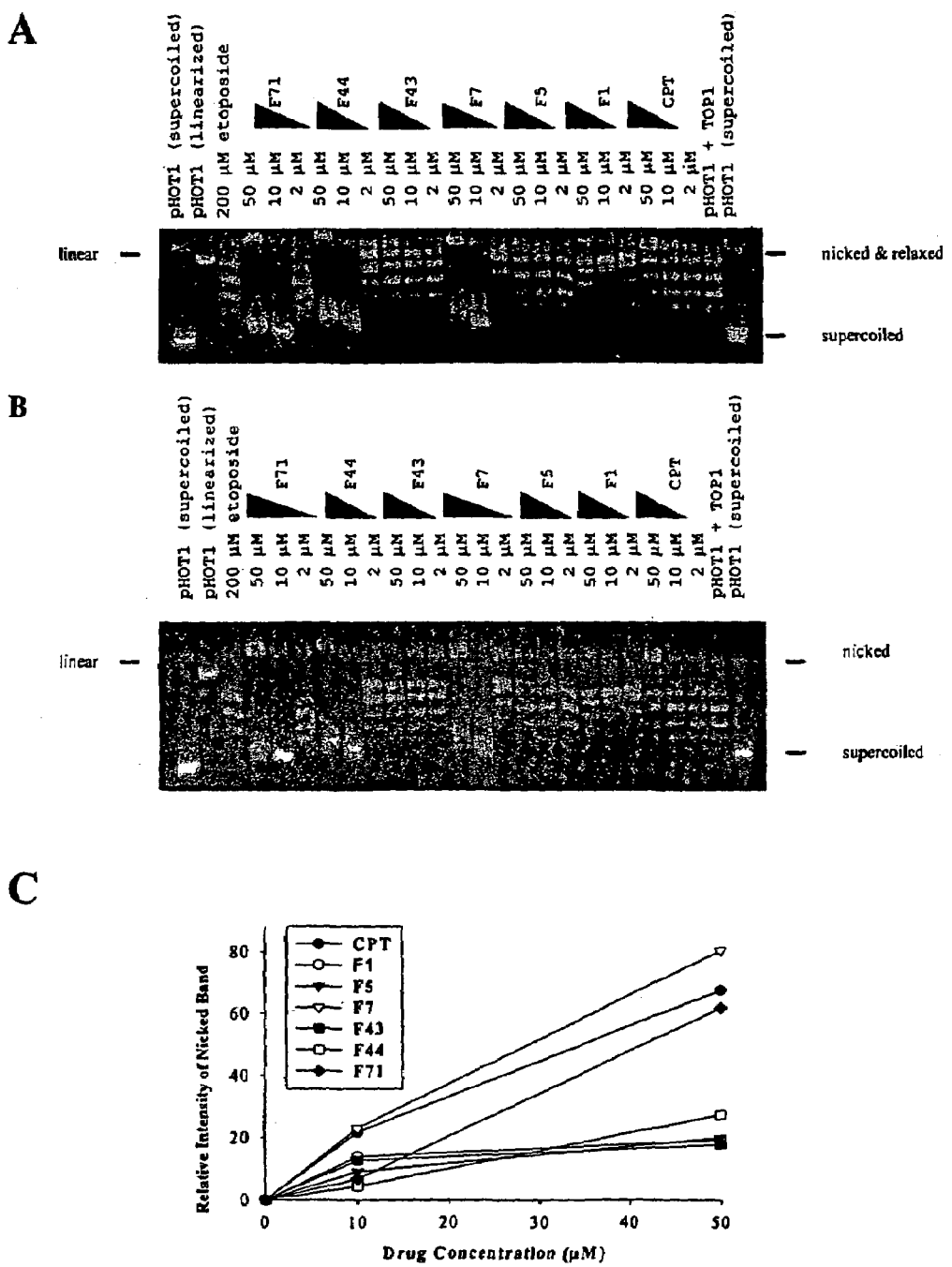
FIGS. 4A, 4B, and 4C shows induction of DNA topoisomerase I (TOP1)-mediated DNA cleavage by various indolocarbazole derivatives and camptothecin (CPT).

In the in vitro system, INDO derivatives and camptothecin were tested for their ability to convert the "supercoiled" form of the pHOT1 DNA substrate into the "nicked" form by stimulating TOP1-mediated DNA breaks in the presence of purified human TOP1. As shown in FIG. 4, in a dose-dependent manner similar to camptothecin, different INDO derivatives induce TOP1-mediated nicking of the pHOT1 plasmid with varying efficiencies. In contrast, used as a negative control, the DNA topoisomerase II-targeted etoposide shows no activity in inducing TOP1-mediated nicking of DNA.

In order to separate the "nicked" from the "relaxed" DNA population, the gel shown in FIG. 4A was further run for 4 h in the presence of ethidium bromide before being photographed as described in the "Methods and Materials." The intensity of the nicked band of each lane of FIG. 4B was quantified as described in the "Materials and Methods." FIG. 4C shows the relative intensity of the nicked band induced by the six INDO derivatives and camptothecin.

As shown in FIG. 4C, the six INDO derivatives can be divided into two groups based on their potency in inducing TOP1-mediated DNA cleavage: the more potent group, consists of F7 and F71, has equivalent activity as camptothecin; and the less potent group, consists of F44, F5, F1 and F43. Interestingly, there is no clear correlation between the radiosensitizing activity and the efficiency in inducing TOP1-mediated DNA cleavage among the tested six INDO derivatives. For example, the radiosensitizing F5 and F1 showed low activities in inducing TOP1-mediated DNA cleavage. On the other hand, the non-radiosensitizing F71 showed potent activity similar to camptothecin in inducing TOP1-mediated DNA cleavage.

Many INDO derivatives have been reported to interact with DNA with a higher affinity than camptothecin (Yoshinari, et al., Cancer Res., 53:490–494 (1993); Bailly, C., et al., Mol Pharmacol., 53:77–87 (1998); and Bailly, C., et al. Mol Pharmacol., 55:377–385 (1999)). Consistent with a stronger interaction between drug molecules and DNA, different INDO derivatives caused varying degrees of "up-shifting" of the supercoiled DNA, as well as alterations in distribution of various DNA topoisomers (FIGS. 4A and 4B).

Example 5

INDO Derivatives Exhibit Varying Efficiencies in Inducing TOP1-Mediated DNA Damage In Vivo The ability to induce the reversible protein-DNA crosslinks, termed the "cleavable complexes," is a unique feature of mammalian TOP1-targeted drugs. Quantitation of the reversible protein-DNA cross-links in cells treated by TOP1-targeted drugs has been used as a measure of the drug molecules that have actually reached their intracellular target. We conducted the potassium-SDS co-precipitation assay to quantify the potency of the six INDO derivatives in trapping the TOP1-DNA complexes in logarithmically growing Chinese hamster CHO cells.

Figure 5:
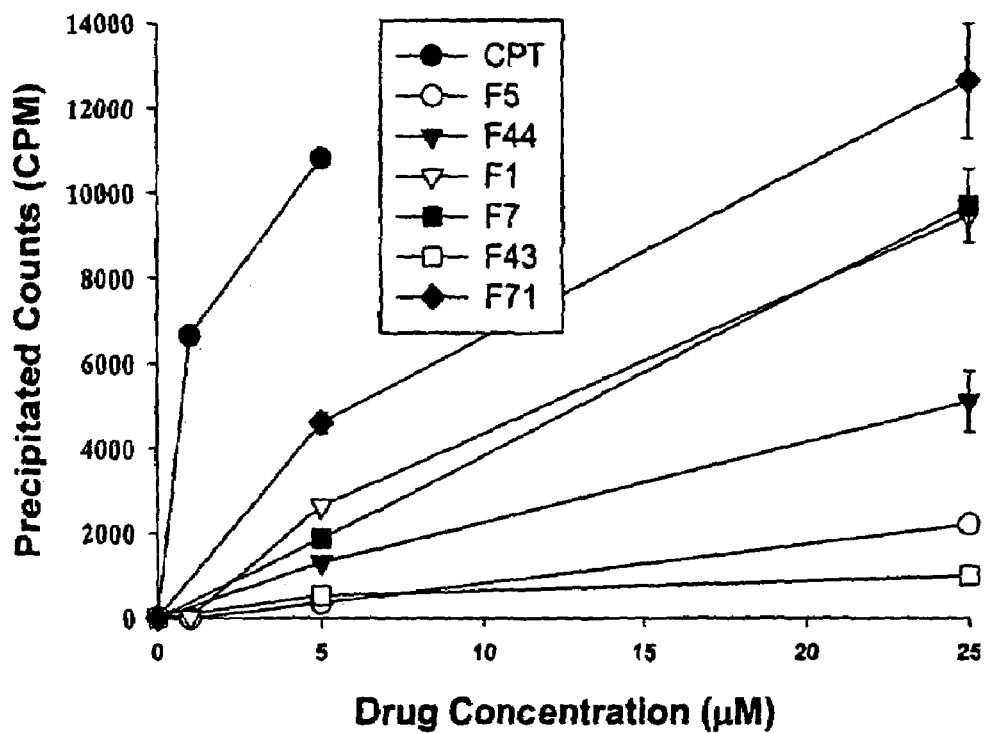
FIG. 5 shows induction of protein-DNA cross-links by various indolocarbazole derivatives and camptothecin (CPT). The formation of covalent topoisomerase-DNA cross-links in CHO cells induced by a 30-min drug treatment was measured by the in vivo $K^+$-SDS co-precipitation assay. The background precipitable counts were obtained by treating the lysate with proteinase K (400 μg/ml) at 65° C. for 2 h. Data are arithmetic means (±SD) of three determinations, and the background counts have been subtracted. Points, mean of triplicates; bars, SD.

As shown in FIG. 5, the potency of the INDO derivatives in stabilizing DNA-protein crosslinks in CHO cells was found to adhere to the following order: F71>F7=F1>F44>F5>F43. As a positive control, camptothecin appears to be the most potent in inducing protein-DNA crosslinks in CHO cells. These drug-induced protein-DNA crosslinks were reversible by dilution or a brief 65° C. heat treatment (data not shown) and most likely represent the TOP1-DNA complexes. There is a good correlation between the potencies in inducing intracellular protein-DNA complexes and the efficiencies to induce TOP1-mediated DNA cleavage among the six INDO derivatives (FIGS. 4C and 5).

This result further indicates that the INDO-induced protein-DNA crosslinks in CHO cells represent the TOP1-DNA cleavable complexes.

Example 6

F71 and F44 are Potent Inducers of TOP1-Mediated DNA Damage and Cytotoxicity, but not RS We investigated the relationship between the TOP1-mediated DNA damage and the cytotoxic and radiosensitizing effects induced by the six INDO derivatives. The cytotoxicity of various INDO derivatives was determined by exposing logarithmically growing human MCF-7, Chinese hamster CHO and DC3F cells to the individual drug for 1 hr, followed by clonogenic survival assays.

As shown in Table 2, based on the $LD_{50}$ (the drug concentration leads to 50% cell death), the order of relative cytotoxic potency of INDO derivatives is as follows: F71, F44>F1, F7>F5, F43. Consistent with the notion that TOP1 is the major cytotoxic target, the cytotoxic potency of the INDO derivative matches well with its efficiency in inducing protein-DNA crosslinks and TOP1-mediated DNA cleavage (Table 2). However, the non-radiosensitizing derivatives F71 and F44 are surprisingly potent inducers of TOP1-mediated DNA damage and cytotoxicity (Table 2). This result indicates an uncoupling between the radiosensitizing activity and the cytotoxic effect in some INDO derivatives.

TABLE 2

The activities in inducing DNA topoisomerase I (TOP1)-mediated DNA damage, cytotoxicity and radiosensitization (RS) of indolocarbazole (INDO) derivatives

| INDO derivatives | TOP1-mediated DNA cleavage[a] | Protein-DNA cross-links[b] | Cytotoxicity[c] | RS[d] |
|---|---|---|---|---|
| F1 | + | ++ | ++ | + |
| F5 | + | + | + | + |
| F7 | +++ | ++ | ++ | + |
| F43 | + | + | + | − |
| F44 | ++ | ++ | +++ | − |
| F71 | +++ | +++ | +++ | − |

[a]Activity of each INDO derivative in inducing TOP1-mediated DNA cleavage in vitro was arbitrarily denoted with "+++" (high activity), "++" (modest activity) and "+" (low activity) based on FIG. 4B and 4C.
[b]Activity of each INDO derivative in inducing covalent protein-DNA cross-links in CHO cells was arbitrarily denoted with "+++" (high activity), "++" (modest activity) and "+" (low activity) based on FIG. 5.
[c]Cytotoxic activity of each INDO derivative is based on the $LD_{50}$ (drug concentration that leads to 50% cell death) determined graphically from clonogenic survival assays using human MCF-7, Chinese hamster CHO and DC3F cells as described in "Materials and Methods." The drug treatment time was 1 h and the cytotoxic activity was arbitrarily denoted with "+++" (high activity, $LD_{50} \leq 4$ μg/ml), "++" (modest activity, $LD_{50} >4$ μg/ml but $\leq 10$ μg/ml) and "+" (low activity, $LD_{50} >10$ μg/ml).
[d]RS activity of each INDO derivative was based on experiments conducted in human MCF-7 (as shown in FIG. 2) and Chinese hamster ovary DC3F cells (as shown in Table 4). "+", possess RS activity; "−", possess no RS activity.

Example 7

Camptothecin-Resistant, TOP1 Mutant DC3F/C-10 Cells Showed Resistance to the Cytotoxic Effect of F7, as Well as the Induction of RS by F7 and F1

The DC3F/C-10 cell line was selected from the Chinese Hamster lung fibroblast DC3F cell line in the presence of 1 μM of camptothecin (Albright, N., Radiat. Res., 112:331–340 (1987), and Chen, Y. N., J. Biol. Chem., 265:10073–10080 (1990)). The amino acid mutation from $Gly^{505}$ to $Ser^{505}$ of the mutant TOP1 has been shown to be responsible for the cell line's camptothecin-resistance phenotype. In an attempt to determine the importance of TOP1 in mediating the cytotoxic and radiosensitizing effects by INDO derivatives, clonogenic survival assays were performed in DC3F and DC3F/C10 cells.

As shown in Table 3, the DC3F/C10 cells showed a more than 12-fold relative resistance (defined as the $LD_{50}$ of DC3F/C10 cells divided by the $LD_{50}$ of DC3F cells) to a 30-min camptothecin treatment. The relative resistance of DC3F/C10 cells to the cytotoxic effect of F7, F44 and F71 were more than 5-fold, 2.5-fold and 2.7-fold, respectively (Table 3). This finding of cross-resistance of the mutant TOP1 to F7, F44 and F71 (Albright, N., Radiat. Res., 112:331–340 (1987), and Chen, Y. N., J. Biol. Chem., 265:10073–10080 (1990)) strongly supports that TOP1 is the cytotoxic target of INDO derivatives. Due to their lack of cytotoxic effect in DC3F and DC3F/C10 cells, the relative resistance of F1, F5 or F43 was not determined (Table 3).

TABLE 3

Cross-resistance pattern of DC3F/C-10 cells to indolocarbazole derivatives

|  | $LD_{50}$[a] | | |
|---|---|---|---|
| Drugs | C3F | C3F/C-10 | RR[b] |
| Camptothecin (μM) | 0.8 | >10 | >12 |
| F1 | >25 | >25 | ND[c] |
| F7 | 4.0 | >20 | >5.0 |
| F44 | 3.2 | 8.0 | 2.5 |
| F71 | 1.5 | 4.1 | 2.7 |

[a]$LD_{50}$, drug concentration that leads to 50% cell death determined graphically from clonogenic survival assay of each drug.
[b]RR (relative resistance) = $LD_{50}$[a] of DC3F/C-10 cells divided by $LD_{50}$[a] of DC3F cells
[c]ND, not determined.

The induction of RS by various INDO derivatives was also examined in the DC3F and DC3F/C-10 cells. As shown in Table 4, in comparison to the DC3F cells, the mutant TOP1 DC3F/C-10 cells showed resistance to induction of RS by F7 and F1. This result suggests that TOP1, in addition to being the cytotoxic target, is also the mediator of the RS induced by F7 and F1. In contrast, consistent with the results in human MCF-7 cells and Chinese hamster CHO cells, F71 and F44 were incapable of inducing RS in both DC3F and DC3F/C10 cells at concentrations as high as 10 μg/ml (data not shown).

TABLE 4

Induction of radiosensitization in DC3F and DC3F/C10 cells by camptothecin, indolocarbazole F1 and F7.

|  |  | DC3F Cells | | DC3F/C10 Cells | |
|---|---|---|---|---|---|
| Drugs |  | Radiation Dose (Gy) at 10% Survival[a] | SER[b] | Radiation Dose (Gy) at 10% Survival | SER |
| No Drug Control |  | 6.0 | 1.0 | 5.2 | 1.0 |
| Camptothecin (μM) | 0.1 | 4.3 | 1.4 | ND[c] |  |
|  | 1.0 | 3.9 | 1.5 | 5.2 | 1.0 |
|  | 10 | ND |  | 4.6 | 1.1 |
| F1 (μg/ml) | 1.0 | 4.9 | 1.2 | ND |  |
|  | 5.0 | 4.6 | 1.3 | 4.8 | 1.1 |
|  | 25 | ND |  | 4.5 | 1.2 |

TABLE 4-continued

Induction of radiosensitization in DC3F and DC3F/C10 cells by camptothecin, indolocarbazole F1 and F7.

| Drugs | DC3F Cells | | DC3F/C10 Cells | |
|---|---|---|---|---|
| | Radiation Dose (Gy) at 10% Survival[a] | SER[b] | Radiation Dose (Gy) at 10% Survival | SER |
| F7 (μg/ml) 2.5 | 4.6 | 1.3 | ND | |
| 5.0 | 3.9 | 1.5 | 5.2 | 1.0 |
| 10 | 3.6 | 1.7 | 4.9 | 1.1 |
| 20 | ND | | 4.1 | 1.3 |

In the present study we characterize the radiosensitizing activity of six INDO derivatives in mammalian cells. Indeed, we showed that three of the six tested INDO derivatives induced RS in mammalian cells. Our results support the notion of TOP1-targeted compounds, in general, as being potential radiation sensitizers.

There are at least two striking features of the radiosensitizing INDO compounds that make them attractive radiation sensitizers. First, the radiosensitizing INDO compounds are potent radiation sensitizers. In the human breast cancer MCF-7 cells, the SERs of F1, F5 and F7 range from 1.7 to 1.9, which is superior to the SER of 1.4 of the potent radiosensitizing camptothecin (Table 1).

Second, the INDO compounds radiosensitize mammalian cells at relatively non-cytotoxic concentrations. "Preferentially non-cytotoxic" is among the major characteristics of an "ideal" radiation modifier for use in combined-modality therapy. Combining non-cytotoxic radiation sensitizers with radiation therapy for treating human cancers provides insurmountable advantages not only in improving the tumor control very selectively over the irradiated area, but also in avoiding the untoward systemic effects of the radiation sensitizer. The locally enhanced normal tissue radiocytotoxicity resulting from the combination of radiosensitizing INDO compounds with radiation is expected to be modest due to the known relatively lower levels of TOP1 in non-malignant cells.

In addition, through careful radiation treatment planning, radiation oncologists can further reduce the potentially increased normal tissue toxicity due to RS effect by using "non-coplanar" radiation fields. Further advantages of using TOP1-targeted radiation sensitizers include the availability of well-established methodologies that can be used to monitor the actual drug concentration reaches the intracellular target of the tumor (Subramanian, D., et al., Cancer Res., 55:2097–2103 (1995), and Pondarre, C., et al., Nucleic Acids Res. 25:4111–4116 (1997)), as well as to determine the appropriate timing of drug delivery and radiation treatment for maximal enhancement (Herscher, L. L., et al., Oncology, 13:11–22 (1999)).

Figure 3:
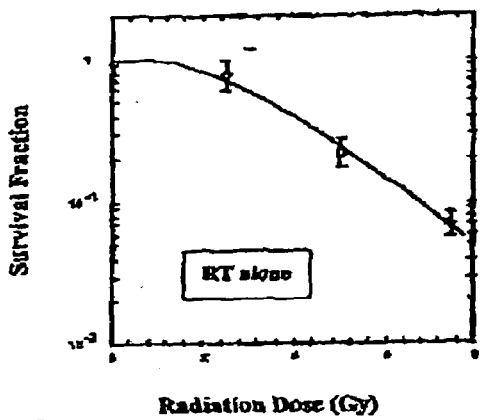
FIG. 3A shows single-hit multitarget (SHMT) survival curves for human MCF-7 cells treated with 1 h incubation with 2 μg/ml of indolocarbazole F1, F5 or F7 followed by radiation (RT).
FIG. 3B shows SHMT survival curve parameters for human MCF-7 cells treated with 1 h incubation with 2 μg/ml of indolocarbazole F1, F5 or F7 followed by radiation (RT). Points, mean of triplicates; bars, SD. $D_0$ and $D_q$ are measurements of the radiation sensitivity of the cells and the width of the shoulder of the survival curve, respectively.
Figure 3:
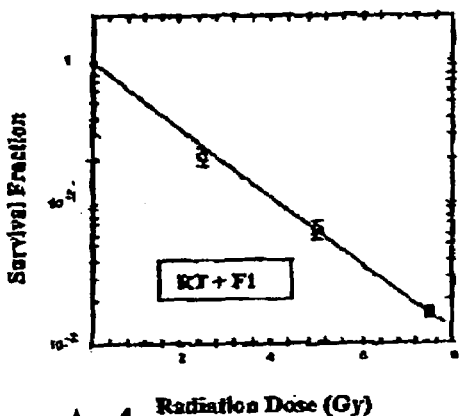
Figure 3:
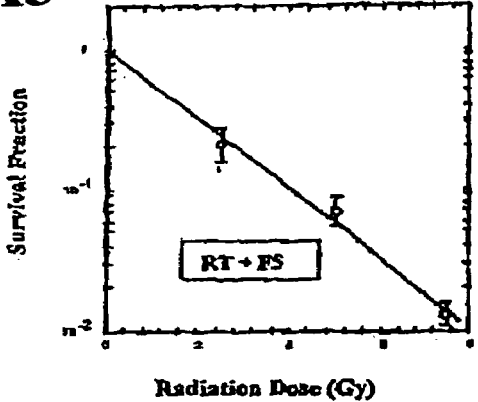
Figure 3:
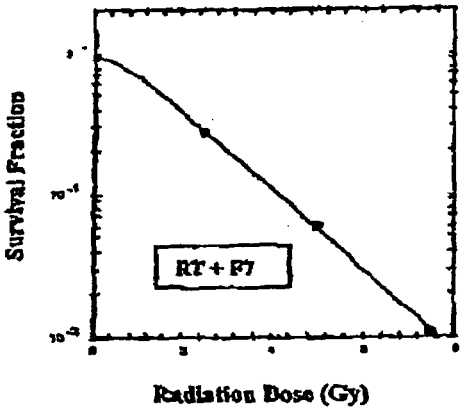

Obliteration of the "shoulder" of the survival curve and not its terminal slope ($1/D_0$) appear to account for the observed RS effect induced by INDO derivatives (FIG. 3). The "shoulder" of the radiation survival curve is often considered as a measure of the repair capacity for "sublethal damage" of the irradiated cells. TOP1 drugs are known to induce DNA breaks by trapping the TOP1-DNA cleavable complexes in actively proliferating cells. The obliteration of the "shoulder" of the radiation survival curve induced by the radiosensitizing INDO derivatives, therefore, is consistent with the theory that these compounds may cause an increase in accumulation of "sublethal DNA damage" through TOP1-mediated mechanism.

It is plausible that such increased accumulation of sublethal DNA damage, which can be readily converted into "lethal" DNA damage with the addition of radiation-induced DNA damage, is responsible for the RS induced by the INDO derivatives. Consistent with this proposed model, our preliminary data have shown that the induction of TOP1-mediated RS depends largely on an intact DNA damage response p53 regulatory pathway (Chen, A. Y., et al., The New York Academy of Sciences, N.Y., in press, 2000).

In an agreement with the published literature, TOP1 appears to be the intracellular mediator for the cytotoxic effects of five out of the six tested INDO derivatives, except F43. First, we have demonstrated that the five TOP1-targeted INDO derivatives exhibit varying efficiencies in inducing TOP1-mediated DNA damages both in vitro and in vivo, which correlate well with their cytotoxic effects (FIG. 4, FIG. 5 and Table 2). Second, the camptothecin-resistant TOP1 mutant DC3F/C10 cells were cross-resistant to the INDO derivatives, including F7, F44 and F71 (Table 3).

The fact that the amino acid mutation from $Gly^{505}$ to $Ser^{505}$ of the mutant TOP1 in DC3F/C10 cells (50,51) confers resistance to INDO derivatives suggest a "similarity" between INDO derivatives and camptothecin in interacting with TOP1 during the trapping of the TOP1-DNA cleavable complexes. This observation is in line with the published work from Bailly et al. showing the camptothecin-resistant TOP1 mutant F361S being cross-resistant to the INDO derivative R-3 (same as F7 of current study) (Pereira, E. R., et al., J. Med. Chem., 39:4471–4477 (1996)). The important role of TOP1 in mediating the RS effects of INDO derivatives is indicated by the resistance of the TOP1 mutant DC3F cells toward induction of RS by F7 and F1 (Table 4).

Interestingly, not all TOP1-targeted INDO derivatives are capable of radiosensitizing cells. The relatively cytotoxic TOP1-targeted F71 and F44 do not induce RS in mammalian cells (Table 2). As previously demonstrated by different researchers, some structural derivatives of INDO possess other biological activities including inhibitory effects toward protein kinase C (Bailly, C., et al., Mol Pharmacol., 55:377–385 (1999), and Bailly, C., et al., J. Med. Chem., 39:4471–4477, (1996)), protein kinase A (35) and TOP1 kinase (Labourier, E., et al., Cancer Res., 59:52–55 (1999); Anizon, F., et al., J. Med. Chem., 40:3456–3465 (1997); Moreau, P., et al., J. Med. Chem., 41:1631–1640 (1998); and Moreau, P., et al., J. Med. Chem., 42:1816–1822 (1999)). The possibility exists that other TOP1-unrelated biological activities of certain INDO derivatives, such as F71 and F44, may interfere with and mask their ability in inducing TOP1-mediated RS. It is also conceivable that RS induction by certain INDO derivatives may be governed by factors different from those known for the induction of TOP1-mediated cytotoxicity.

In summary, we have demonstrated that some INDO derivatives enhance radiation cytotoxicity at relatively non-cytotoxic concentrations. TOP1 appears to be the mediator for their cytotoxic, as well as radiosensitizing, effects. Our results confirm the important role of TOP1 in mediating RS and strongly suggest the future development of INDO derivatives as a new class of radiation sensitizers.

Although the invention has been described with reference to the presently preferred embodiment, it should be understood that various modifications can be made without departing from the spirit of the invention. Accordingly, the invention is limited only by the following claims.

What is claimed is:

1. A method for enhancing the effect of radiation in the treatment of breast cancer comprising administering to a subject in need of such treatment a radiosensitivity increasing amount of an indolocarbazole derivative having the following structure A

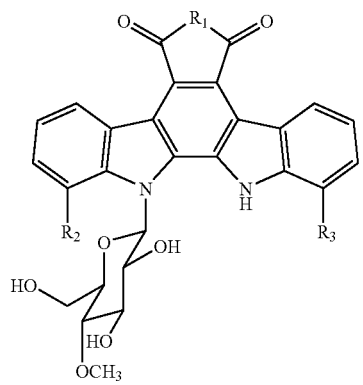

wherein $R_1$ is not $NCH_3$ and wherein $R_2$ and $R_3$ are not H when $R_1$ is NH; and wherein the subject is treated with radiation and the amount of indolocarbazole derivative is at a non-cytotoxic level corresponding to the effect obtained in MCF-7 cell culture using said indolocarbazole derivative at a concentration of at least 1, 2, 5 or 10 ug/ml, but not exceeding 10 ug/ml.

2. The method of claim 1, wherein $R_1$ is NH, O, or NOH.

3. The method of claim 1, wherein $R_2$ and $R_3$ are Cl or H.

4. The method of claim 1, wherein the indolocarbazole derivative is administered before the subject is treated with radiation.

5. The method of claim 1, wherein the indolocarbazole derivative is administered while the subject is treated with radiation.

6. The method of claim 1, wherein the indolocarbazole derivative is administered in a pharmaceutical composition.

* * * * *